US005850458A

United States Patent [19]

Tomisawa et al.

[11] Patent Number: 5,850,458

[45] Date of Patent: Dec. 15, 1998

[54] APPARATUS AND METHOD FOR ACTIVELY REDUCING NOISE IN VEHICULAR PASSENGERS COMPARTMENT

[75] Inventors: Naoki Tomisawa; Shigeo Ohkuma, both of Atsugi, Japan

[73] Assignee: Unisia Jecs Corporation, Atsugi, Japan

[21] Appl. No.: 429,500

[22] Filed: Apr. 26, 1995

[30] Foreign Application Priority Data

| | | | |
|---|---|---|---|
| Apr. 28, 1994 | [JP] | Japan | 6-091446 |
| Oct. 21, 1994 | [JP] | Japan | 6-256728 |

[51] Int. Cl.$^6$ .......... A61F 11/06

[52] U.S. Cl. .......... 381/71.4; 381/71.5

[58] Field of Search .......... 381/71, 86, 71.5, 381/71.4, 71.1, 71.3, 94.1; 415/119

[56] References Cited

U.S. PATENT DOCUMENTS

| | | | |
|---|---|---|---|
| 4,783,817 | 11/1988 | Hamada et al. | 381/71.5 |
| 4,805,733 | 2/1989 | Kato et al. | 381/71.5 |
| 5,018,202 | 5/1991 | Takahashi et al. | 381/71 |
| 5,063,598 | 11/1991 | Geddes | 381/71.5 |
| 5,111,507 | 5/1992 | Nakaji | 381/71 |
| 5,221,185 | 6/1993 | Pla et al. | 381/71 |
| 5,222,148 | 6/1993 | Yuan | 381/71 |
| 5,245,664 | 9/1993 | Kinoshite et al. | 381/71 |
| 5,325,437 | 6/1994 | Doi et al. | 381/71 |
| 5,337,365 | 8/1994 | Hamabe et al. | 381/71 |
| 5,384,853 | 1/1995 | Kinoshita et al. | 381/71 |
| 5,410,605 | 4/1995 | Sawada et al. | 381/71 |
| 5,426,705 | 6/1995 | Yokota et al. | 381/71 |
| 5,446,790 | 8/1995 | Tanaka et al. | 381/71 |
| 5,485,523 | 1/1996 | Tamamura et al. | 381/71 |
| 5,502,869 | 4/1996 | Smith et al. | 381/71.5 |

FOREIGN PATENT DOCUMENTS

| | | |
|---|---|---|
| 3908881 | 3/1990 | Germany . |
| 4221292 | 1/1993 | Germany . |

OTHER PUBLICATIONS

Paul A. Lynn, "The Discrete and Fast Fourier Transforms", *Digital Signal Processing,* pp. 211–247, May 1990.

*Primary Examiner*—Vivian Chang
*Attorney, Agent, or Firm*—Foley & Lardner

[57] ABSTRACT

In an apparatus and method for actively reducing air intake noise of an air intake system of a vehicular internal combustion engine, a sound wave having approximately the same amplitude, and a phase shifted by 180° from the air intake sound wave, is generated from a sound wave generator to cancel the air intake sound, which is unpleasant to vehicular occupants.

33 Claims, 16 Drawing Sheets

APPARATUS AND METHOD FOR ACTIVELY REDUCING NOISE IN VEHICULAR PASSENGERS COMPARTMENT

BACKGROUND OF THE INVENTION

The present invention relates to an apparatus and method for actively reducing noise propagated in a vehicular passenger compartment and generated from an air intake system of a vehicular engine, through mutual sound wave interference between the noise generated from the air intake system noise due to air intake pulsation and an acoustic cancellation sound wave.

U.S. Pat. No. 5,111,507 issued on May 5, 1992 (which corresponds to European Patent Application No. 90308078.6), U.S. Pat. No. 5,245,664 issued on Sep. 14, 1993 (which corresponds to a German Patent No. 40 421 16), U.S. Pat. No. 5,410,604 issued on Apr. 25, 1995, U.S. Pat. No. 5,337,365 issued on Aug. 9, 1995 (which corresponds to a German Patent Application First Publication No. DE 42 28 695 A1), U.S. Pat. No. 5,325,437 issued on Jun. 28, 1994 (which corresponds to a German Patent Application First Publication No. DE 42 44 108 A1), U.S. patent application Ser. No. 08/026,151 filed on Mar. 3, 1993 (now allowed, and which corresponds to a German Patent Application First Publication No. DE 43 06 638 A1), and U.S. Pat. No. 5,384,853 issued on Jan. 24, 1995 (which corresponds to a German Patent Application First Publication No. DE 43 98 923 A1) exemplify conventional passenger compartment active noise reduction systems.

However, these previously proposed noise reduction systems generally reduce noise propagated from engine combustion, vehicular suspension systems, differential gears, and/or wind noises.

SUMMARY OF THE INVENTION

It is therefore a principal object of the present invention to provide an apparatus and method for actively reducing noise generated from an air intake system of a vehicle engine due to air intake pulsation to a sufficient level through active noise reduction whereby a sound wave having approximately an equal amplitude and an opposite phase of the air intake noise is generated to cancel the air intake noise. This avoids the need for an elongation and/or dimension enlargement of an air intake duct or for installation of a special resonator in the air intake system to attenuate the air intake noise.

The above-described object can be achieved by providing an active noise reducing apparatus for an automotive vehicle, comprising: a) an air intake signal generator disposed in an air intake system of a vehicular engine, for generating an air intake signal representative of the air intake sound wave; b) a signal processor for setting a frequency, an amplitude, and a phase of a cancellation signal for canceling the air intake noise; and c) a sound wave generator for generating a sound wave on the basis of the cancellation signal.

The above-described object can also be achieved by providing an active noise reducing method for an automotive vehicle, comprising a) generating an air intake signal representative of an air intake sound wave; b) setting a frequency, amplitude, and phase of a cancellation signal for canceling the air intake signal; and c) generating a sound wave on the basis of the cancellation signal.

BEST MODE FOR CARRYING OUT THE INVENTION

Figure 1:
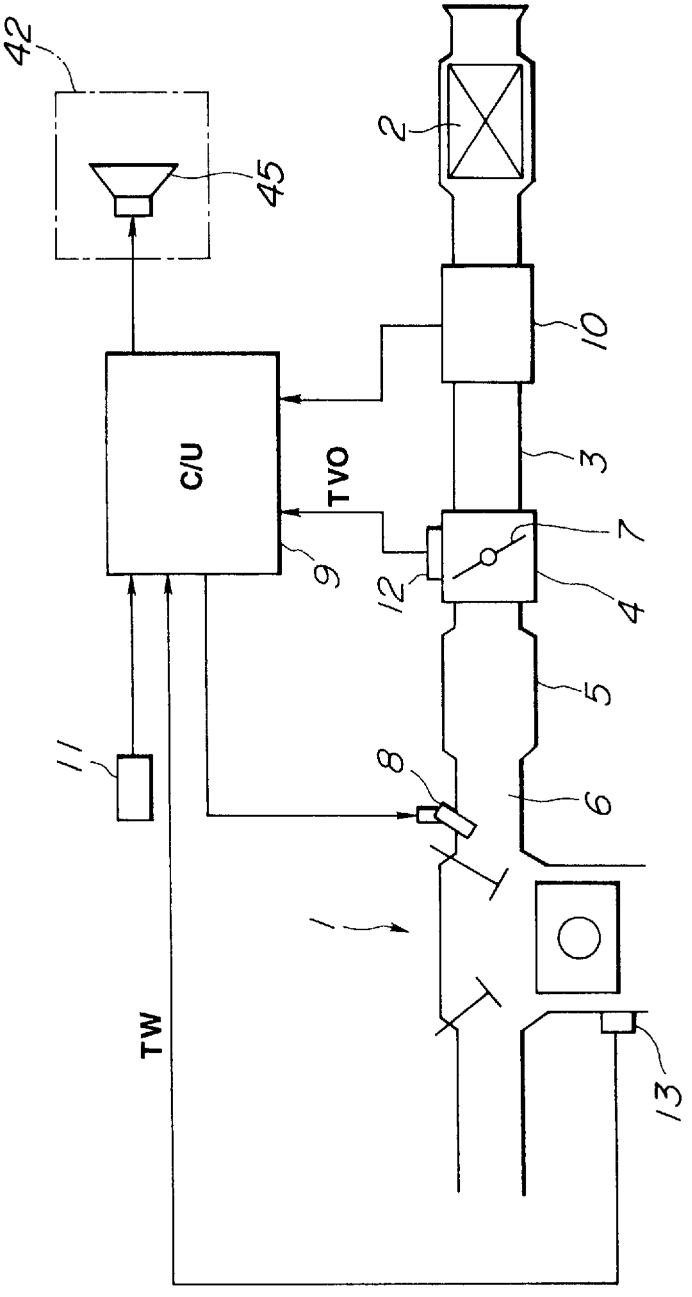
FIG. 1 is a schematic circuit block diagram of an apparatus for actively reducing noise generated from an air intake system of a vehicular engine in a first preferred embodiment according to the present invention.

Reference will hereinafter be made to the drawings in order to facilitate a better understanding of the present invention. FIG. 1 shows a system configuration of an apparatus for reducing noise generated from an air intake system of a vehicular internal combustion engine in a first preferred embodiment according to the present invention.

The engine 1 includes an air cleaner 2, an air intake duct 3, a throttle chamber 4, an air intake collector 5, and an air intake manifold 6 through which air is drawn into the engine cylinders.

The throttle chamber 4 is provided with a throttle valve 7 associated with an accelerator such as an accelerator pedal (not shown) for adjusting the air intake quantity supplied to the engine 1.

Branched portions of the air intake manifold 6 are provided with a plurality of electromagnetic coil type fuel injection valves 8 corresponding to respective cylinders. Each fuel injection valve 8 injects fuel pressurized at a predetermined pressure by means of a pressure regulator into the air intake manifold 6, the fuel being supplied from a fuel pump (not shown).

Each fuel injection valve 8 is driven intermittently in response to a fuel injection quantity signal supplied from a control unit 9. The fuel injection quantity Ti is controlled according to a pulsewidth of the fuel injection quantity signal calculated and output from the control unit 9.

An airflow meter 10 is installed in a part of the air intake duct 3 located upstream of the throttle chamber 4 so as to detect the intake air quantity Qa of the engine 1.

It is noted that the airflow meter 10 detects the air intake mass flow quantity Q drawn into the engine 1 on the basis of, for example, a variation in the resistance value of a heat sensitive resistor disposed within the air intake duct 3. Such an airflow meter type is disclosed in U.S. patent application Ser. No. (not yet assigned) filed on Feb. 22, 1995 having the priorities based on two Japanese Patent Application Nos. JP 6-150429 and JP 6-54624 (attorney docket No. 32926/915), the content of which is incorporated herein by reference.

It is noted that when the heat sensitive resistor type airflow meter is used, air streams opposite to the forward air stream are sensed in the same way as the forward air stream. Thus, the opposite air streams are represented in an output signal produced by the airflow meter 10, allowing detection of amplitudes and frequencies of air intake ripples with high accuracy. Or alternatively, another type of airflow meter which does not respond to the opposite air stream may be used.

A crank angle sensor 11 is disposed on the engine crankshaft or engine cam shaft to produce an engine revolution signal. The control unit 9 calculates an engine revolution speed Ne on the basis of the engine revolution signal from the crank angle sensor 11.

An engine coolant temperature sensor 13 is installed in the engine 1 to generate a temperature signal representative of the temperature TW of engine coolant. A throttle sensor 12 is installed on the throttle valve 7 to generate a signal representative of opening angle TVO of the throttle valve 7.

Figure 2A:
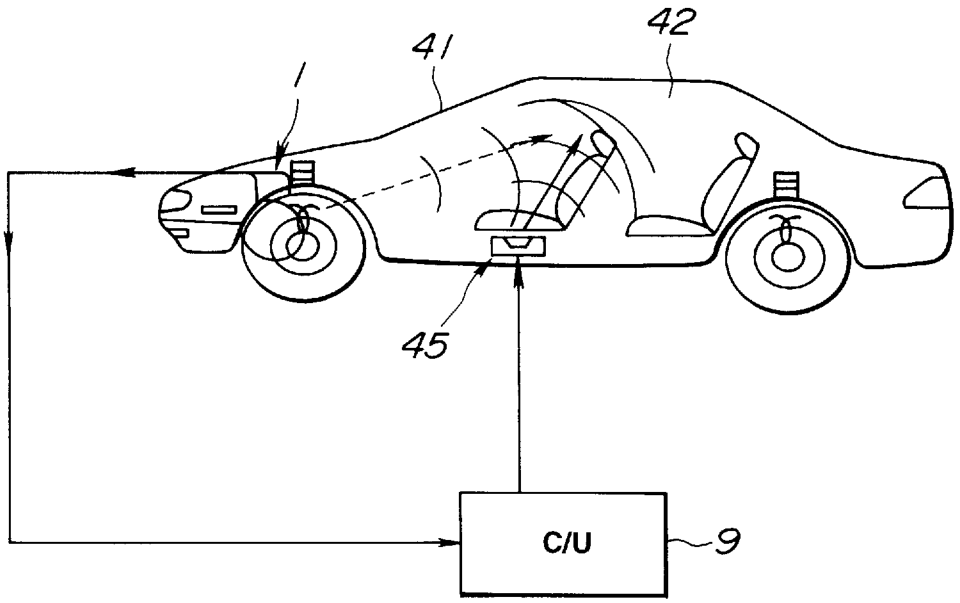
FIG. 2A is a schematic explanatory view of an arrangement of a sound wave generator in the first embodiment shown in FIG. 1.
Figure 2B:
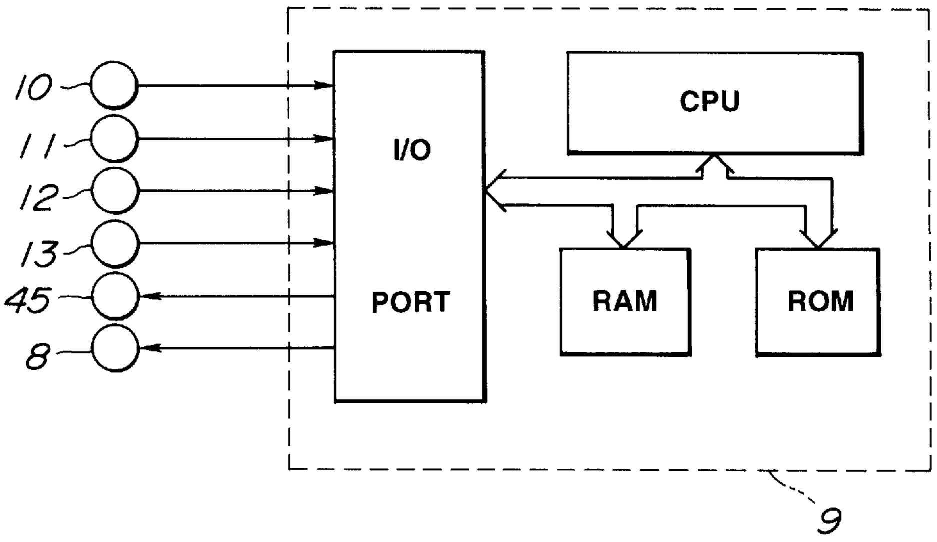
FIG. 2B is a schematic circuit block diagram of a control unit shown in FIG. 1.

FIG. 2B shows an internal circuit of the control unit 9. The control unit 9 generally includes a microcomputer having a CPU, RAM, ROM, I/O port, and a common bus.

The control unit 9 calculates an initial fuel injection quantity pulsewidth Tp on the basis of the signal from the airflow meter 10 and signal from the crank angle sensor 11, corrects the initial fuel injection quantity pulsewidth Tp in accordance with correction coefficients related to engine conditions such as the engine coolant temperature TW to yield a final fuel injection quantity pulsewidth Ti, and outputs a drive signal having a pulsewidth corresponding to the final fuel injection quantity pulsewidth Ti to a corresponding fuel injection valve in synchronization with engine revolution.

The control unit 9 may also function as a control unit for the active noise reducing apparatus in the first embodiment according to the present invention.

FIG. 2A shows an arrangement of the active noise reducing apparatus in the first embodiment according to the present invention.

A sound wave generator such as a speaker 45 is disposed on a floor located below the front seat of a passenger compartment 42 of an automotive vehicle 41.

The speaker 45 is driven under the control of the control unit 9, to generate a cancellation sound wave for canceling noises propagated into the vehicle passenger compartment. The speaker 45 constitutes a transducer which converts an electrical signal into acoustic energy, for example, a vibrator or an oscillator such as a piezoelectric element.

Figure 3:
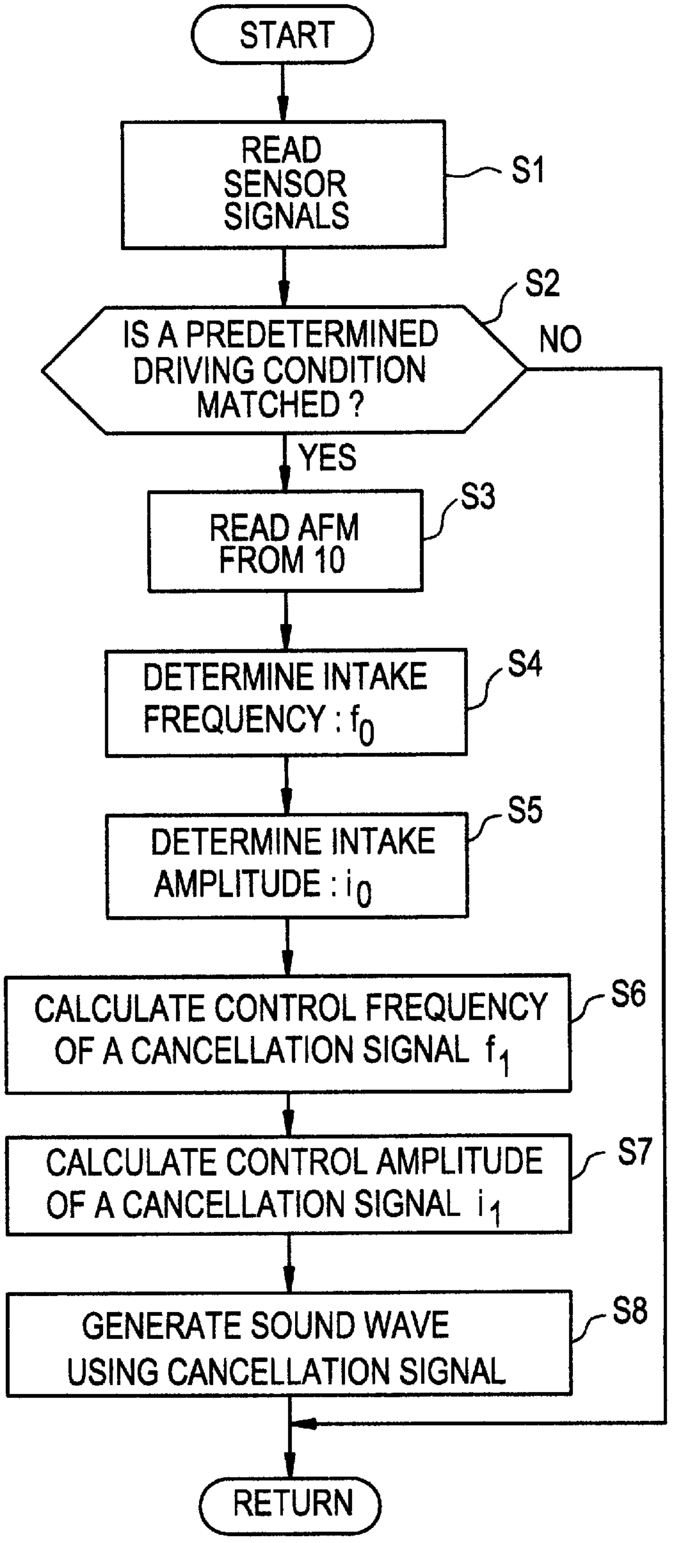
FIG. 3 is an operational flowchart indicating an active noise reduction control process executed in the control unit shown in FIG. 1.

FIG. 3 shows an operational flowchart representing an active noise reduction control process using the speaker 45 which is executed in the control unit 9 in the first embodiment.

At step S1, the CPU of the control unit 9 reads the opening angle TV0 of the throttle valve 7 from the signal provided by throttle valve opening angle sensor 12, the engine revolution speed Ne calculated on the basis of the crank angle signal from the crank angle sensor 11, the engine coolant temperature TW from the signal provided by the coolant temperature sensor 13, and air intake quantity Qa from the signal AFM provided by the airflow meter 10.

At step S2, the CPU determines whether the engine driving condition matches a predetermined engine driving condition in which noise from the air intake system contributes significantly to noise propagated in the passenger compartment. The determination is made on the basis of the sensor signals.

Such a predetermined engine driving condition could be, for example, an engine revolution speed Ne equal to or above 2000 rpm and a variation rate ΔTV0 of the opening angle TVO of the throttle valve 7 is 30°/sec. If a predetermined engine driving condition is matched at step 52, the CPU determines that the air intake sound wave is large enough to generate air intake noise in the passenger compartment and the control process proceeds to step 53.

At step S3, the CPU reads the signal AFM of the airflow meter 10.

At step S4, the CPU measures a number of points at which a first-order differential value of the signal AFM is zero within a unit of time, and detects an air intake pulsation frequency $f_0$. These points are defined for the purposes of the invention, as times at which the signal AFM is reversed due to air intake pulsation.

It is noted that where the air intake sound wave includes a pulsation, the signal AFM from the airflow meter 10 accordingly represents the pulsation. Analysis of the pulsation in the ripple signal AFM at step S4 permits detection of the air intake ripple frequency $f_0$ of the pulsation.

At step S5, the CPU carries out a peak-and-hold operation on the signal AFM of the airflow meter 10 within a duration corresponding to a predetermined crank angular displacement to calculate an air intake pulsation amplitude $i_0$.

At a step S6, the CPU calculates a frequency $f_1$ of a cancellation signal for generating a sound wave to be output from the speaker 45. It is noted that the canceling frequency $f_1$ has the same frequency value as the frequency $f_0$ detected at step S4 such that $f_1=f_0$. It is also noted that the phase of the cancellation frequency $f_1$ is deviated by 180° from that of the air intake pulsation.

At step S7, the CPU calculates an amplitude $i_1$ of the cancellation signal for generating a sound wave to be output from the speaker 45. It is noted that the amplitude $i_1$ has the same amplitude as the air intake pulsation amplitude $i_0$ derived at the S5 such that $i_1=i_0$.

At the next step S8, the CPU drives the speaker 45 with the cancellation signal having the frequency $f_1$ calculated at step S6 and the amplitude $i_1$ calculated at step S7.

The speaker 45 is thereby driven so as to produce a sound wave for canceling the air intake sound wave.

Therefore, it is possible, in the first embodiment, to generate a sound wave for canceling air intake noise to prevent disturbance in the passenger compartment 42. Hence, it is not necessary to extend the air intake duct 3 or to install a resonator in the air intake system of the engine 1 for reducing air intake noise. Consequently, the cost of the air intake system components is reduced and layout in an engine compartment of the vehicle 41 can be improved.

In the first embodiment, no microphone to transduce the sound energy of the air intake noise into electrical energy is used, and so the whole system is simplified and the cost of the active noise reducing apparatus is reduced.

In addition, in place of measurement of the number of points at which the first-order differential value of the output signal AFM is zero per unit time at step S4, the CPU may use a Fourier transform for determination of the frequency and amplitude of the pulsation component of the signal AFM of the airflow meter 10.

Figure 4:
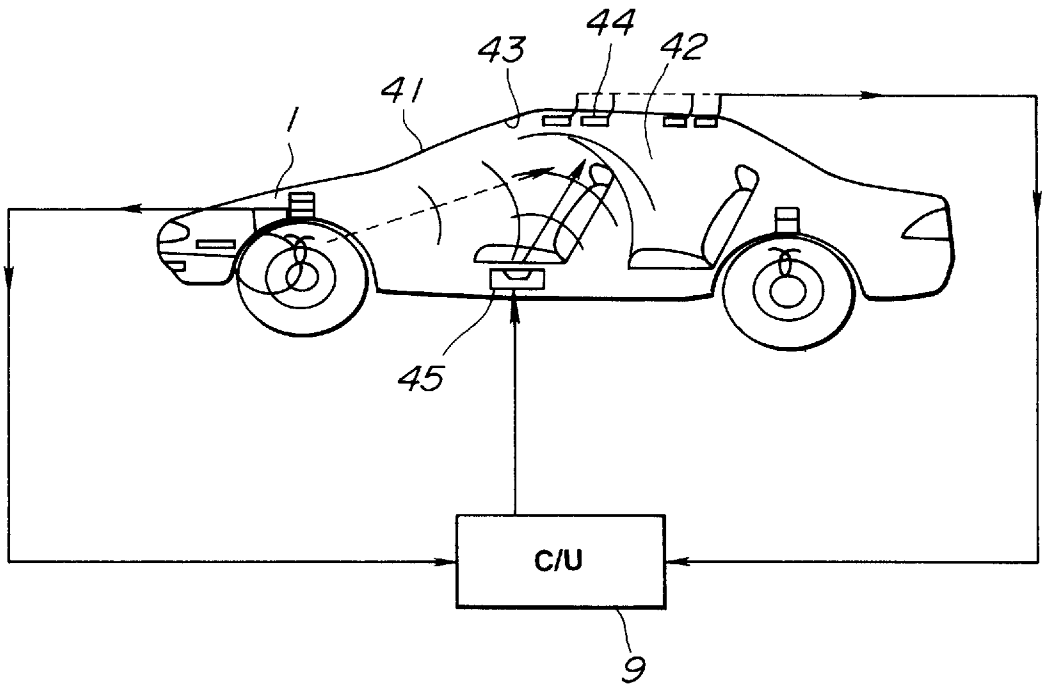
FIG. 4 is a schematic view of arrangements of a speaker and a microphone in a second preferred embodiment of the active noise reduction apparatus according to the present invention.

FIG. 4 shows an arrangement of a plurality of microphones in the automotive vehicle 41 in a second preferred embodiment of the active noise reducing apparatus according to the present invention.

It is noted that the whole configuration of the active noise reducing apparatus is generally the same as in the first embodiment shown in FIGS. 1 and 2B.

However, in the second embodiment, four microphones 44 are disposed at positions at the rear 43 of a ceiling trim within the passenger compartment 42 overhead of the positions of passenger seats. These microphones 44 can transduce the acoustic wave within the passenger compartment into a corresponding electrical signal.

The control unit 9 determines, using a performance function stored in the memory of the control unit 9, whether cancellation of air intake noise by means of the sound wave generated from the speaker 45 disposed below the front passenger seats is sufficient on the basis of the residual sound wave detected by the microphones 44, and corrects the cancellation signal (hereinafter called corrective control).

Figure 5:
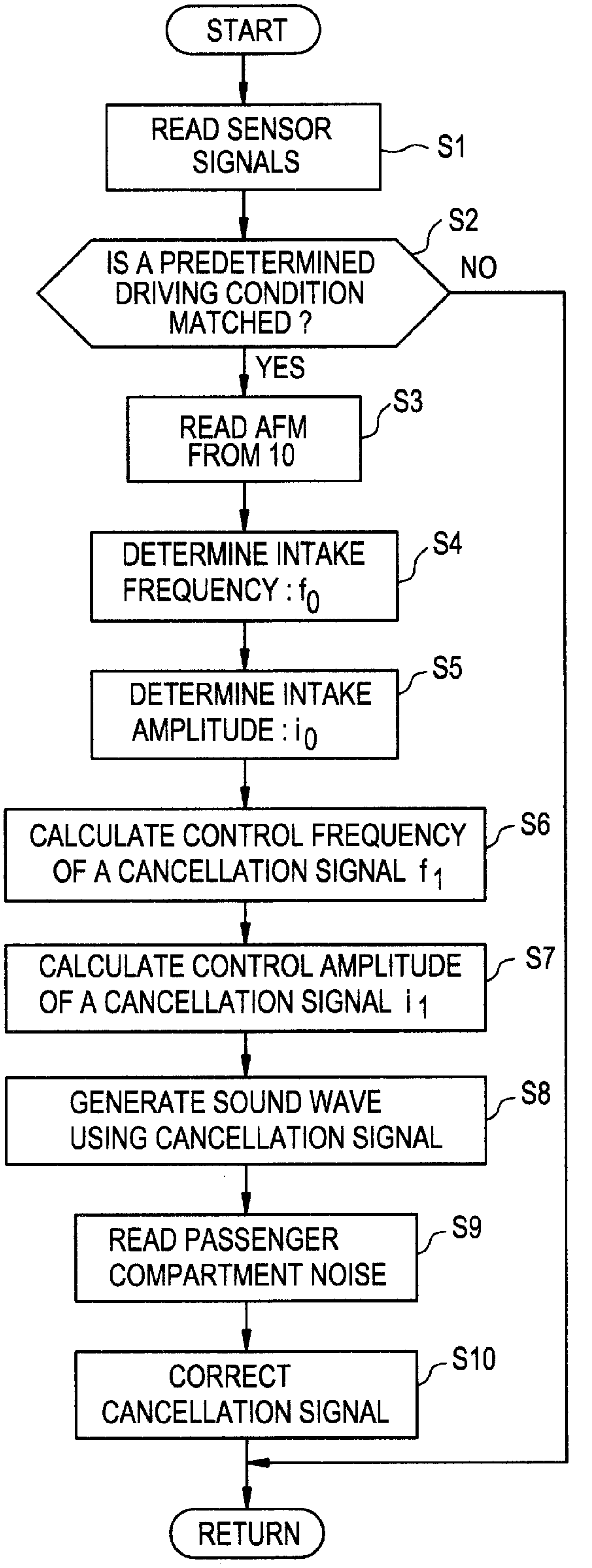
FIG. 5 is an operational flowchart indicating the active noise reduction control executed in the control unit shown in FIG. 4.

FIG. 5 shows the active noise control and corrective control routine executed by the control unit 9 in the second embodiment. The performance function is exemplified by U.S. Pat. Nos. 5,337,365 and 5,325,437, the disclosures of which are incorporated herein by reference.

It is noted that the contents of the steps shown in FIG. 3 and discussed in regard to the first embodiment are the same for the corresponding steps of FIG. 5.

At step S9, the CPU reads a residual sound wave in the passenger compartment while the sound wave corresponding to the cancellation signal is generated from the speaker 45 to cancel the air intake noise in the passenger compartment 42.

At step S10, the CPU analyzes the signals provided by the microphones 9 using a frequency spectrum analyzer of the control unit 9 to determine whether the sound wave generated by the speaker 45 sufficiently cancels air intake pulsation, and corrects the frequency $f_1$, amplitude $i_1$, and phase of the cancellation sound wave on the basis of the determination result described above. Specifically, any of the frequency, amplitude, and phase of the cancellation signal may be corrected to lower the amplitude of air intake pulsation noise in the passenger compartment.

In the active noise reducing apparatus in the third embodiment, a sound wave generator such as a speaker 45 is disposed on or in the air intake system of the engine 1 so that the air intake noise due to air intake pulsation is canceled at the noise generation source before propagation of the air intake noise into the passenger compartment 42.

Figure 6:
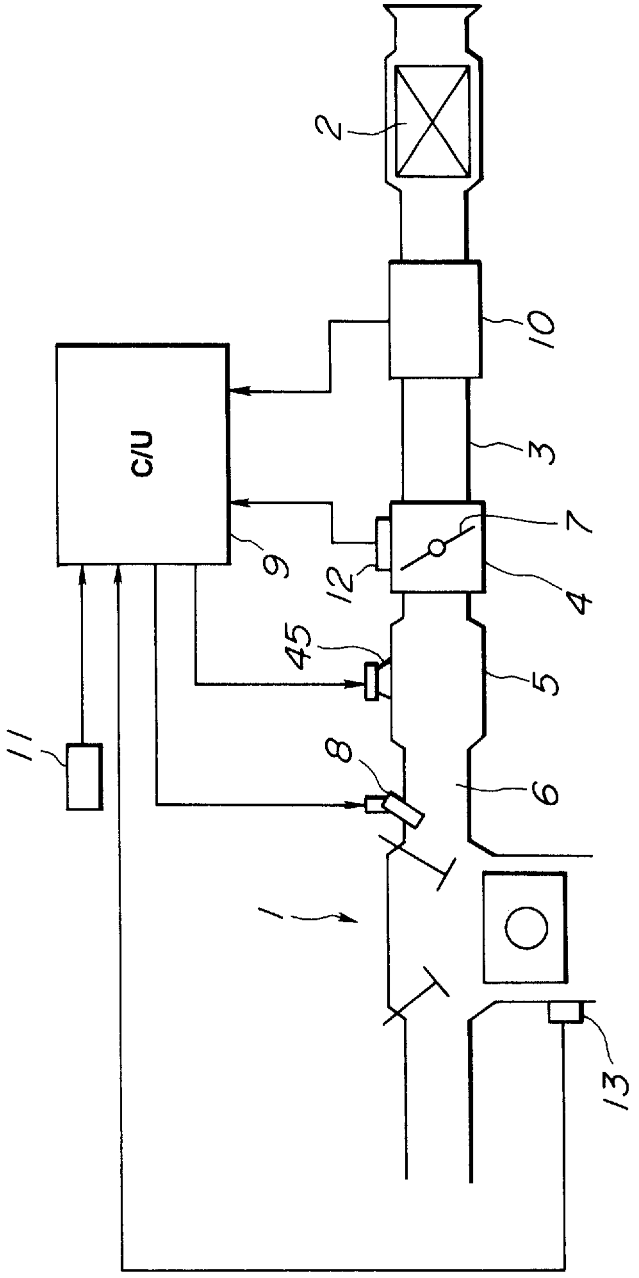
FIG. 6 is a schematic circuit block diagram of the active noise reducing apparatus in a third preferred embodiment according to the present invention.

FIG. 6 shows a system configuration of the active noise reducing apparatus in the third embodiment according to the present invention.

It is noted that in the third embodiment, in which the speaker 45 is disposed at the air intake system of the engine 1, the speaker 45 may be disposed downstream of the throttle chamber 4 as shown in FIG. 6, provided that the speaker 45 is sufficiently small. However, if a relatively large-sized speaker 45 is used, it is preferable for the speaker 45 to be disposed in the vicinity of the air cleaner 2. It is noted that since the whole configuration of the active noise reducing apparatus shown in FIG. 6 is the same as that shown in FIG. 1 except the arrangement of the speaker 45, the detailed explanation thereof is herein.

In the third embodiment, the sound wave for canceling the air intake noise is generated in proximity to the position for detection of the air intake pulsation, and so cancellation of the air intake noise can be achieved outside of the environment of the passenger compartment 42.

In addition, since it is not necessary to install the speaker 45 within the passenger compartment 42, the passenger compartment 42 can more effectively be used for another purpose.

It is possible in the third embodiment to combine the feature in the second embodiment with the third embodiment, such that corrective control is added to the active noise reducing apparatus in the third embodiment.

Figure 7:
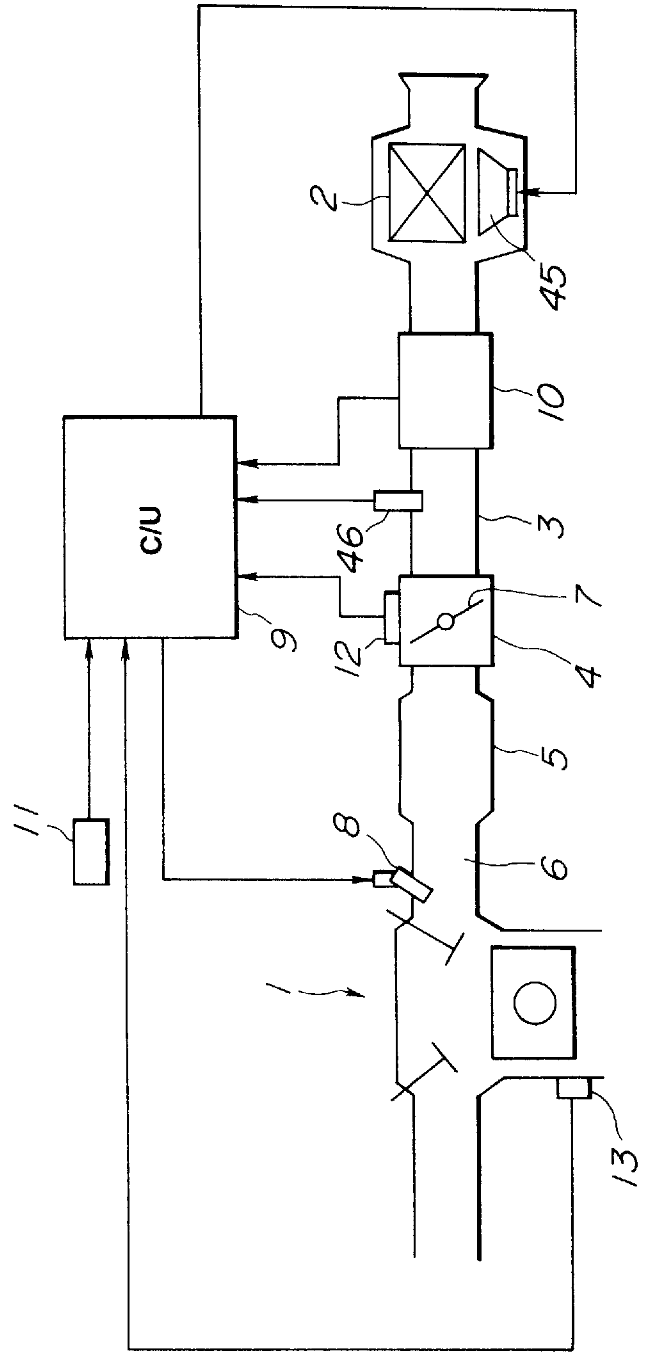
FIG. 7 is a schematic circuit block diagram of the active noise reducing apparatus in a fourth preferred embodiment according to the present invention.

FIG. 7 shows a system configuration of the active noise reducing apparatus in a fourth preferred embodiment according to the present invention.

Since the same reference numerals shown in FIG. 7 as those shown in FIG. 1 are like elements designated in the first embodiment, the detailed explanations are omitted herein.

In the fourth embodiment, a single speaker 45 is disposed on a wall near the air cleaner 2, and a single microphone 46 is disposed on a wall of the air intake duct 3 located upstream of the throttle valve 7 for detecting sound within the air intake duct 3.

The microphone 46 transduces the sound wave within the air intake duct 3 to produce a signal representative of an air intake sound wave.

Figure 8:
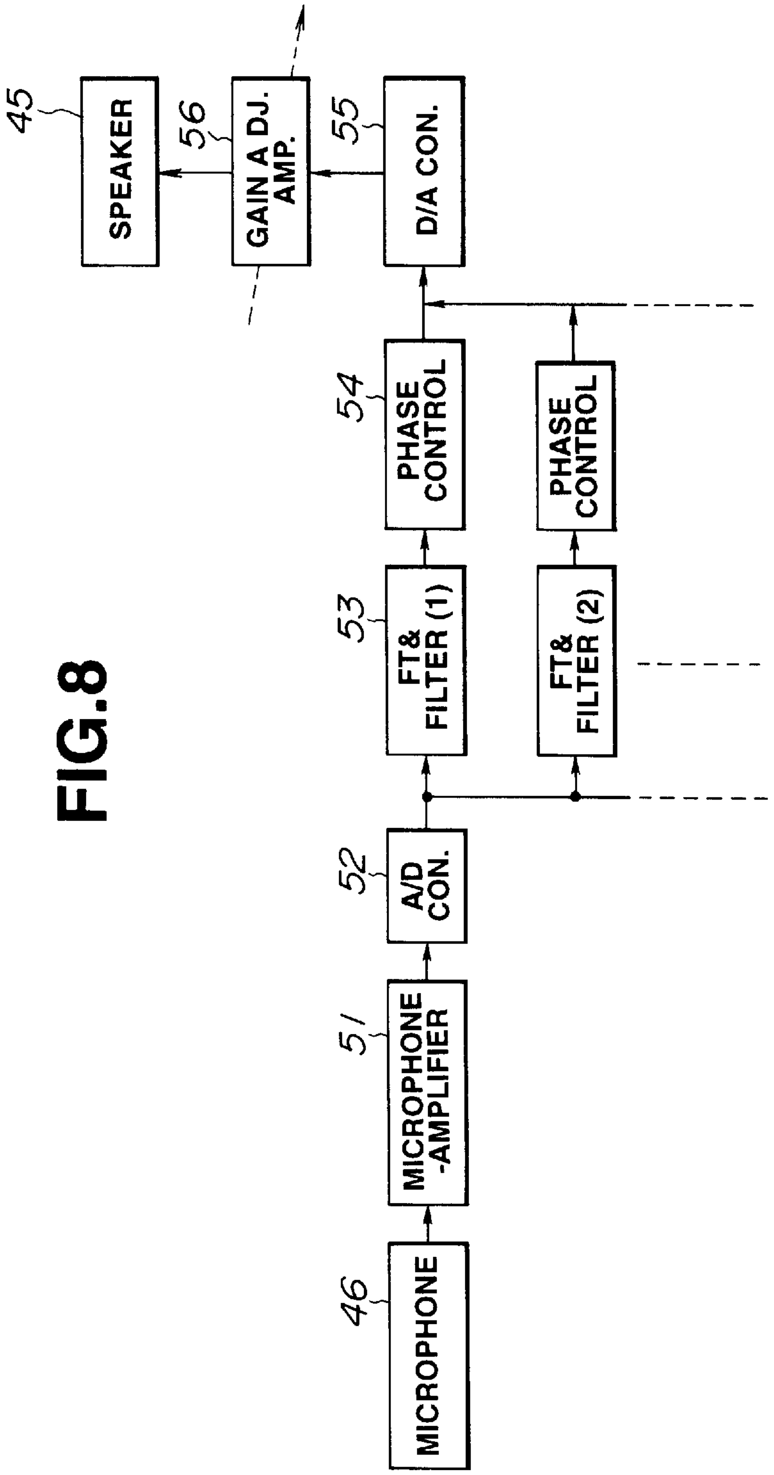
FIG. 8 is a functional block diagram of the active noise reducing apparatus in the fourth embodiment shown in FIG. 7.

FIG. 8 shows a functional block diagram of the active noise reducing apparatus in the fourth embodiment shown in FIG. 7.

In the control unit 9 of the fourth embodiment, the air intake signal is processed by a microphone amplifier 51 and an A/D converter 52 to produce a digital signal.

A plurality of digital filters 53 (1), (2) are provided within the control unit 9.

Each of the digital filters serves to analyze a frequency component of the digital signal from the A/D converter 52. A phase control portion 54 is connected in series with each digital filter 53. Each phase control portion 54 serves to perform a phase control for the corresponding frequency component. The signals produced by the phase controls are converted into corresponding analog signals by means of a D/A converter 55. Finally, the analog signal derived from the D/A converter 55 is output to the speaker 45 whose outlet is faced against the air cleaner 2 via a power amplifier 56. Thus, a sound wave having the same amplitude as the air intake sound wave generated within the air intake duct 3 and having a phase shifted by 180° from the air intake sound wave is generated from the speaker 45 so that the air intake sound wave is canceled within the air intake duct 3.

Figure 9:
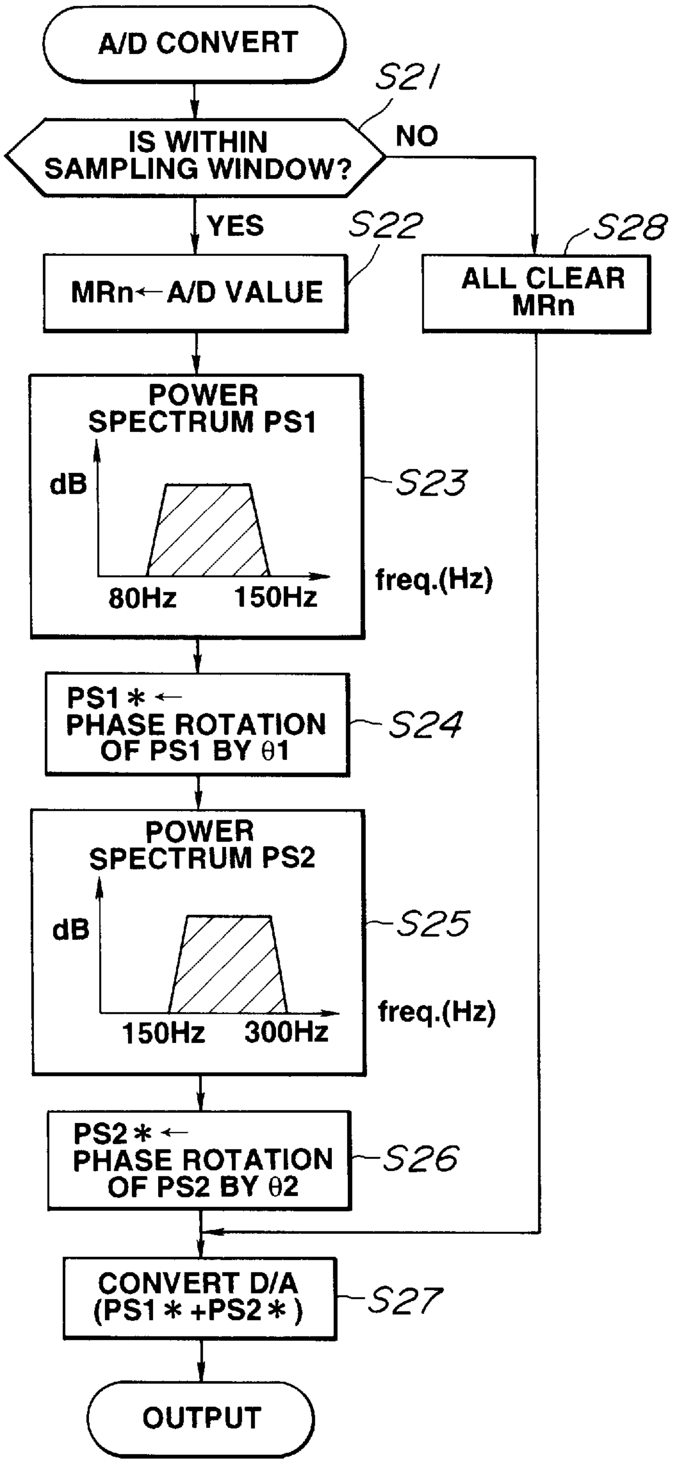
FIG. 9 is an operational flowchart for explaining the active noise reduction control in the fourth embodiment shown in FIGS. 7 and 8.

FIG. 9 shows an operational flowchart executed in the fourth embodiment shown in FIGS. 7 and 8.

At step S21, the CPU receives the signal from the A/D converter 52, and the CPU determines whether the air intake sound wave signal from the microphone 46 falls within a predetermined sampling window. If the electrical signal from the microphone 46 is within the predetermined sampling window (Yes) at step S21, the routine goes to step S22 in which the value of the digital signal within the predetermined sampling window i.e., $MR_n$ (n=1, 2, 3, . . . ) is sequentially stored into memory, for example, a RAM of the control unit 9.

Figure 10:
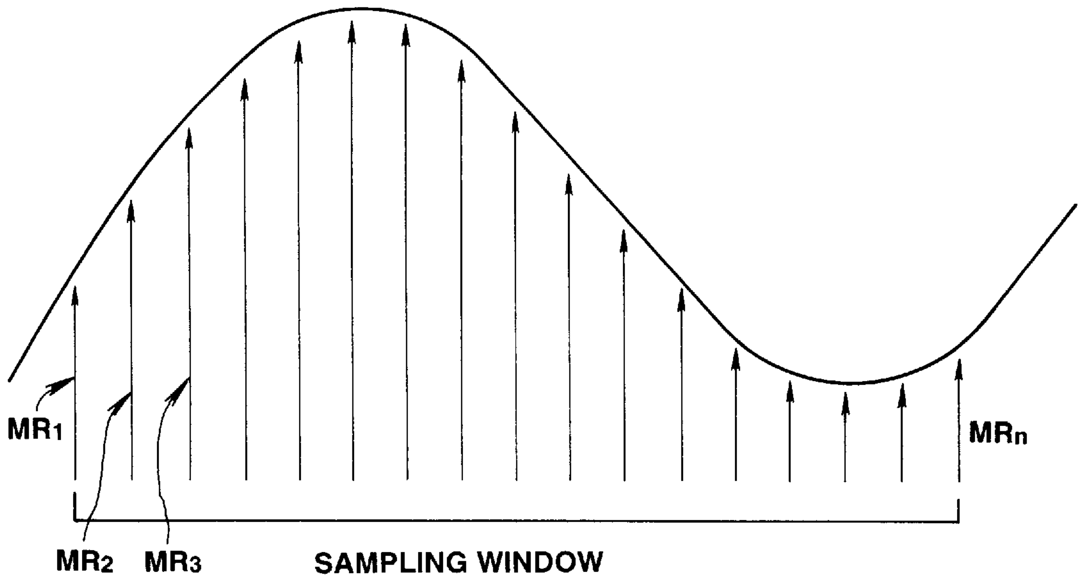
FIG. 10 is a characteristic graph for explaining a sampling window for an output signal from a microphone in the fourth embodiment shown in FIGS. 7 and 8.
Figure 11:
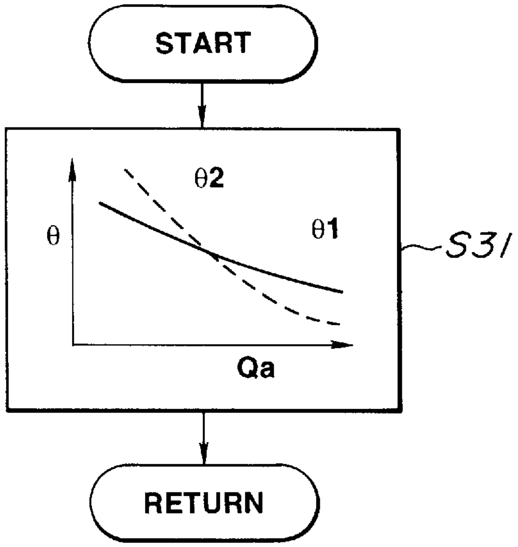
FIG. 11 is an operational flowchart indicating a phase control executed in a fifth preferred embodiment of the active noise reducing apparatus according to the present invention.

FIG. 10 shows the predetermined sampling window used in step S22. The sampling rate is fixed as shown in FIG. 11 in accordance with a sampling formula.

On the other hand, if, at step S21, the air intake sound wave signal does not fall within the predetermined sampling window (No), namely, exceeds the predetermined sampling window, the routine goes to step S28. At step S28, all of the values of $MR_n$ read at the previous sampling window are cleared so that a new data at the subsequent sampling window is may be stored in the RAM.

When the air intake sound wave signal is converted into the corresponding digital signal which falls within the predetermined sampling window and is stored in the RAM, at step S23, the CPU carries out a Fourier transform for the n-th number of data collected within the predetermined sampling window so as to extract a predetermined frequency component (for example, 80 Hz through 150 Hz), thus providing a power spectrum PS1 as shown in FIG. 9. Step S23 is carried out at the digital filter (1) 54 shown in FIG. 8.

At step S24, phase control is provided such that a phase of the predetermined frequency component is shifted by a first predetermined angle θ1 for canceling air intake noise for each of the extracted frequency components.

Next, at step S25, the CPU extracts frequency components in a frequency range different from that of the frequency components analyzed at step S23 (for example, 150 Hz through 300 Hz) (power spectrum PS2 shown in FIG. 9). At the next step S26, the CPU carries out phase control such that the phase of the corresponding frequency component at step S25 is shifted by a second predetermined angle $\theta_2$ to cancel air intake noise at the corresponding frequency.

Then, at step S27, the CPU synthesizes each frequency component for which phase control is carried out (PS1*+ PS2*) and, thereafter, the digital-to-analog conversion is carried out to provide an analog cancellation signal for driving the speaker 45 disposed within the air intake duct 3.

It is noted that the first and second predetermined angle values θ1 and θ2 are fixed, in the fourth embodiment, to 180° so as to generate a sound wave having a phase 180° opposite to that of the air intake sound wave.

However, in order to avoid a variation in the noise canceling effect due to variance of the air intake quantity or air intake velocity, the above-described first and second predetermined angle values θ1 and θ2 may be varied according to the magnitude of the air intake quantity and/or air intake velocity.

Thus, a fifth preferred embodiment in which the values of θ1 and θ2 are set in accordance with the air intake quantity and a sixth preferred embodiment in which the values of θ1 and θ2 are set in accordance with the air intake velocity will be described below.

FIG. 11 shows an operational flowchart indicating the settings of the first and second predetermined angle values θ1 and θ2 in the fifth embodiment of the active noise reducing apparatus.

The structure of the fifth embodiment is the same as that in the case of the fourth embodiment shown in FIGS. 7 through 10. However, the settings of θ1 and θ2 are different from those in the case of the fourth embodiment.

At step S31, the CPU sets the first and second predetermined angle values θ1 and θ2 in accordance with the air intake quantity Qa detected by means of the airflow meter 10, respectively. Even if the same air intake quantity Qa is derived, different angles θ are given for different frequency components to be subjected to phase control. As shown in FIG. 11, the value of θ1 and θ2 is reduced as the air intake quantity Qa is increased.

Figure 12:
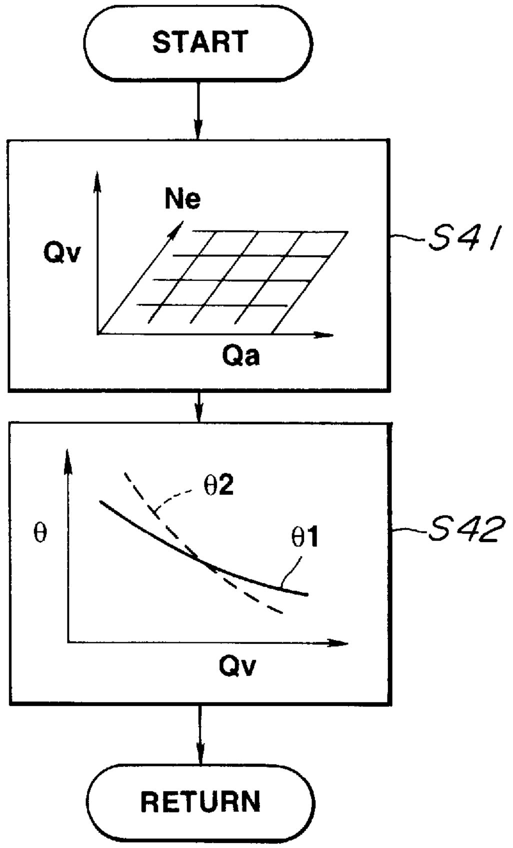
FIG. 12 is an operational flowchart indicating the phase control executed in a sixth preferred embodiment of the active noise reducing apparatus according to the present invention.

FIG. 12 shows an operational flowchart indicating a determination of the intake air velocity and the derivations of the values of θ1 and θ2 in accordance with the value of the air intake velocity in a sixth preferred embodiment according to the present invention.

The structure of the active noise reducing apparatus in the sixth embodiment is the same as that in the case of the fourth embodiment shown in FIGS. 7 through 10.

Referring to FIG. 12, at step S41, the CPU determines the air intake velocity Qv on the basis of the air intake quantity Qa detected by the airflow meter 10 and the calculated engine revolution speed Ne using a table look-up technique shown in FIG. 12.

At the next step S42, the first and second predetermined values of θ1 and θ2 are set according to the air intake velocity Qv. Even if the same intake air velocity Qv is determined, different angles of θ may be applied to different extracted frequency components.

As described in the fourth embodiment shown in FIG. 9, the intake air sound wave is analyzed into two different frequency components to drive the speaker 45. Alternatively, three or more frequency components may be analyzed to allow for variations of the air intake waveform. However, the burden of calculation becomes large when the number of frequency components to be analyzed is increased.

It is noted that the main cause of air intake noise is air intake pulsation. If the frequency of the air intake pulsation which varies according to the engine driving condition can be specified, it is possible to converge the frequency range of the frequency components to be analyzed according to the output signal of the microphone 46. Such a convergence of the frequency range as described above reduces the calculation burden while enabling more accurate calculation of the air intake noise.

Figure 13:
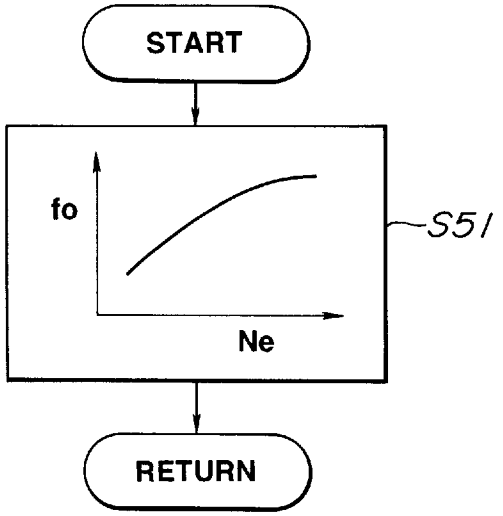
FIG. 13 is an operational flowchart indicating a setting control of an analyzed frequency in a seventh preferred embodiment of the active noise reducing according to the present invention.

FIG. 13 shows an operational flowchart indicating the specification of the frequency range described above in accordance with the engine revolution speed Ne in a seventh preferred embodiment of the active noise reducing apparatus according to the present invention.

The structure of the active noise reducing apparatus in the seventh embodiment is the same as that in the case of the fourth embodiment.

That is to say, at step S51, the CPU of the control unit 9 sets a center frequency $f_0$ using the engine revolution speed signal Ne which is correlated to the frequency of the air intake pulsation.

Then, the CPU extracts a frequency component within the frequency range having a predetermined width including the center frequency $f_0$, and carries out phase control for the extracted frequency component to drive the speaker 45.

Figure 14:
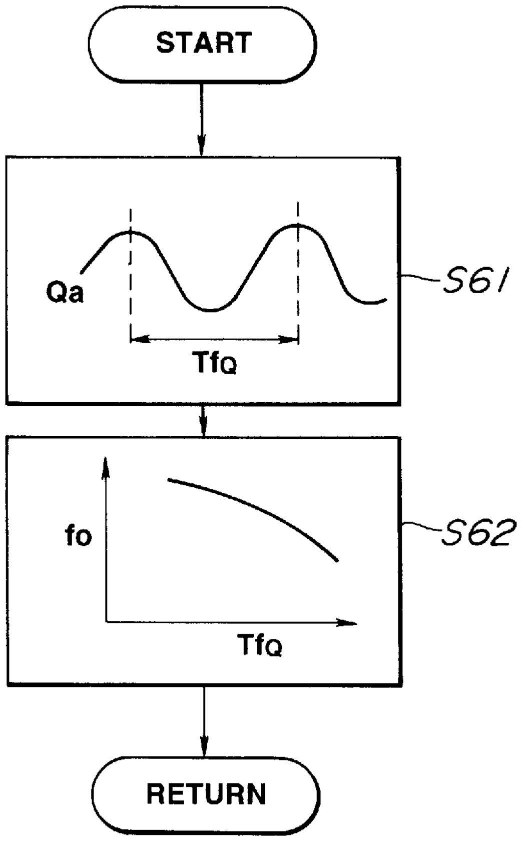
FIG. 14 is an operational flowchart indicating the setting control of the analyzed frequency in an eighth preferred embodiment of the active noise reducing apparatus according to the present invention.

FIG. 14 shows an operational flowchart indicating the specification of the frequency range described above in a case of an eighth preferred embodiment of the active noise reducing apparatus.

The structure of the active noise reducing apparatus in the eighth embodiment is the same as that in the case of the fourth embodiment.

Referring to FIG. 14, the CPU at step S61 determines a variation period $Tf_Q$ of the air intake quantity Qa detected by the airflow meter 10, i.e., the period of air intake pulsation.

At step S62, the CPU sets the center frequency $f_0$ according to the determined variation period $Tf_Q$ at step S61.

Thereafter, the same processing as in the case of the seventh embodiment is carried out.

As described above in the case of the fourth, fifth, sixth, seventh, and eighth embodiments, the microphone 46 disposed in or on the air intake system of the engine 1 serves to detect the air intake sound wave and a signal is generated from the speaker 45 for canceling the intake air sound. Thus, the effect of sound cancellation is provided through attenuation of air intake pulsations which is the main cause of air intake noise.

Hence, the effect of air intake noise cancellation can be evaluated on the basis of the amplitude of air intake pulsation detected by the airflow meter 10. Then, the characteristics of the cancellation sound wave generated from the speaker 45 are corrected through evaluation of the cancellation effect. Consequently, the effect of the air intake noise cancellation can be optimized.

In a ninth preferred embodiment and tenth embodiment, active noise reduction control for the air intake sound wave along with corrective control is provided as described below.

Figure 15:
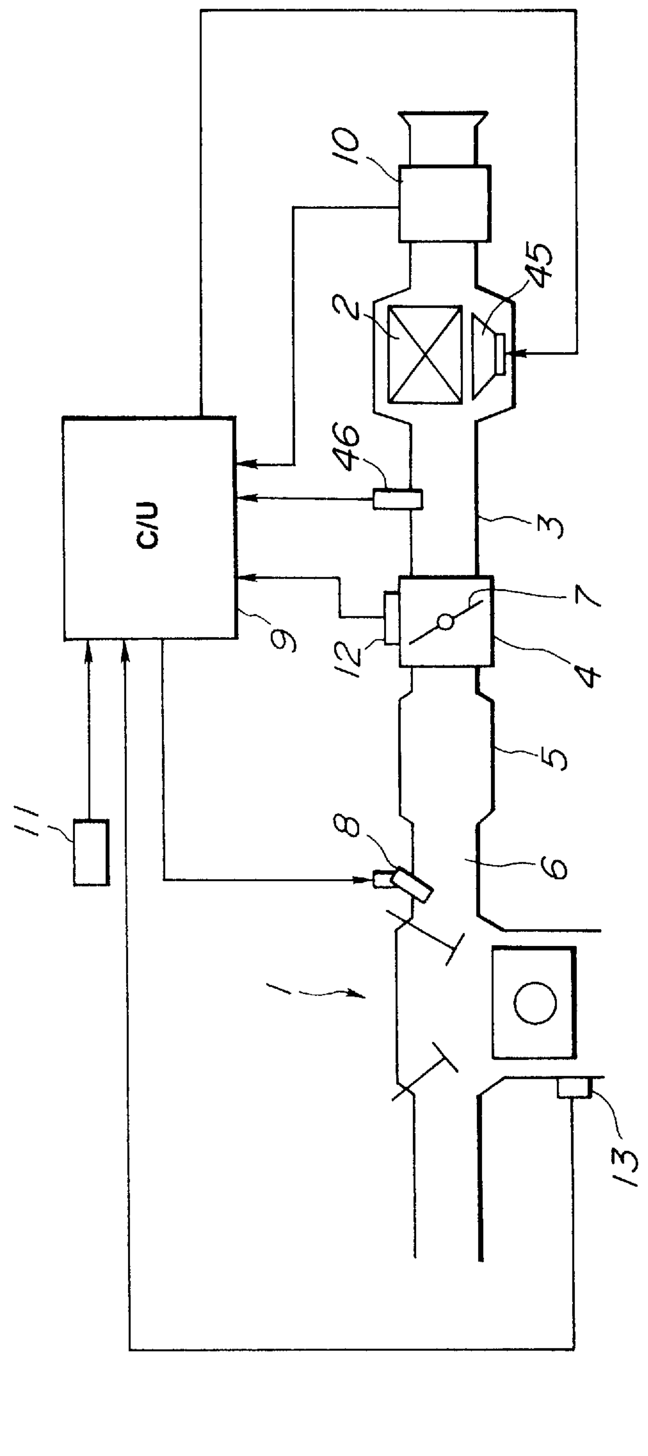
FIG. 15 is a schematic circuit block diagram of the active noise reducing apparatus in both of ninth and tenth preferred embodiments according to the present invention.

FIG. 15 shows a system configuration of the active noise reducing apparatus in the ninth preferred embodiment according to the present invention.

It is noted that the structure of the tenth embodiment of the active noise reducing apparatus is the same as shown in FIG. 15.

The microphone 46 is disposed in the air intake system downstream of the air cleaner 2, the speaker 45 is disposed in the air intake system of the engine 1 near the air cleaner 2 so as to face against the air cleaner 2, and the airflow meter 10 is disposed upstream of the air cleaner 2, as shown in FIG. 15.

This is because, for detection of the air intake sound wave by the microphone 46, placement in proximity to the generation source of the air intake sound wave avoids disturbance caused by other sources. In addition, it is desirable to evaluate the effect of air intake noise cancellation at a position between the speaker 45 and an air intake inlet of the air intake duct 3, which is a source of the air intake noise.

Although in the ninth and tenth embodiments shown in FIG. 15, the air cleaner 2 is disposed between the microphone 46 and airflow meter 10 with the air cleaner 2 being integrated with the speaker 45, the air cleaner 2 may be disposed further upstream of the airflow meter 10 in order to prevent the temperature-sensitive resistor of the airflow meter 10 from damage.

Figure 16:
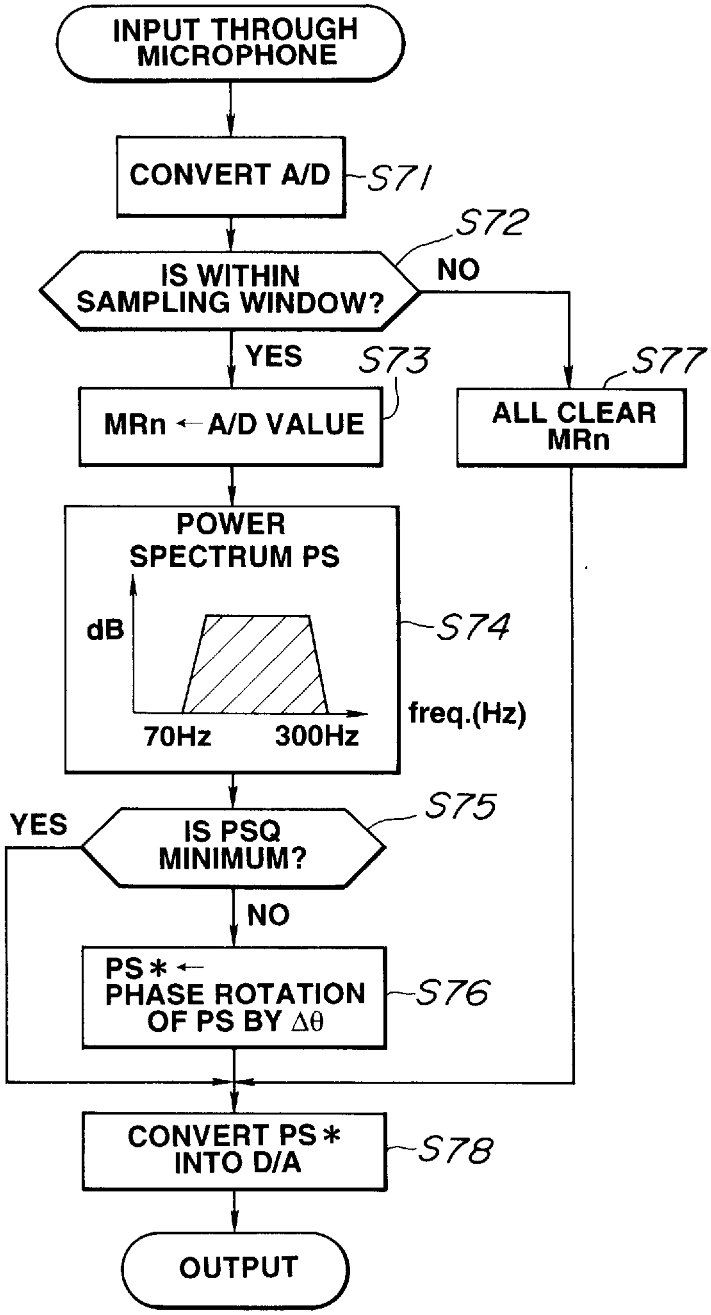
FIG. 16 is an operational flowchart indicating the active noise reduction control executed in the ninth embodiment shown in FIG. 15.
Figure 17:
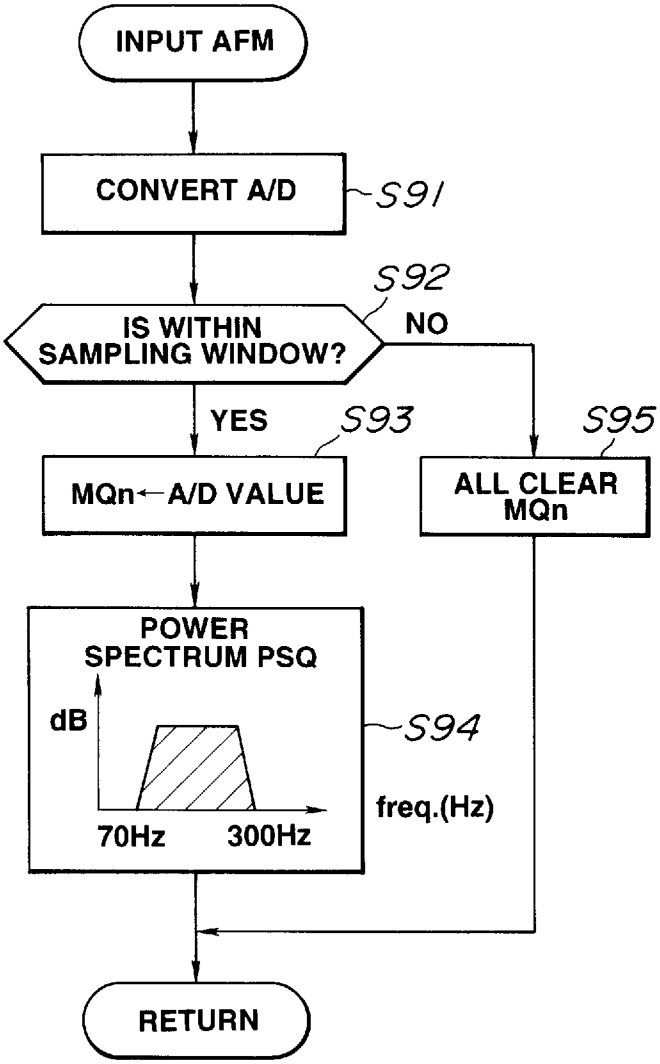
FIG. 17 is another operational flowchart indicating the active noise reduction control executed in the ninth embodiment shown in FIG. 15.

FIGS. 16 and 17 show operational flowcharts executed in the ninth embodiment shown in FIG. 15.

Referring to FIG. 16, at step S71, the CPU reads the digital signal from the A/D converter.

At step S72, the CPU determines whether the digital signal falls within the predetermined sampling window.

If the digital signal is within the predetermined sampling window, the routine goes to step S73. At step S73, the digital signal is sequentially stored in the RAM as data $MR_n$ (n=1, 2, 3, . . . ).

On the other hand, if the digital signal is not within the predetermined sampling window, the routine goes to step S77 in which the data of $MR_n$ stored at the previous sampling window are cleared.

At step S73, the output MRn is derived within the predetermined sampling window and, thereafter, the routine goes to step S74 in which the CPU extracts predetermined frequency components within a predetermined frequency band (for example, 70 Hz through 300 Hz) using the Fourier transform so as to derive the power spectrum PS.

It is noted that the Fourier transform method is exemplified by an English document titled Introductory Digital Signal Processing, authored by Paul A. Lynn, Chapter 7, reprinted in January, 1992, the content of which is incorporated herein by reference. It is also noted that the power spectrum is also called a frequency spectrum i.e., the distribution of the amplitude (and sometimes the phase) of the frequency components of a signal, as a function of frequency (refer to the New IEEE Standard Dictionary of Electrical and Electronics Terms, ISBN 1-55937-240-0 SH15594, published on Jan. 15, 1993).

Next, at step S75, the CPU determines whether an amplitude (power spectrum PSQ) of the frequency components from the air intake represented in the signal from the airflow meter 10, the same as those of the power spectrum PS, is minimum.

If, at step S75, the CPU determines that the amplitude described above is not minimum, the routine goes to step S76.

At step S76, the CPU executes phase control such that phases of the frequency components in the power spectrum PS are shifted by $\Delta\theta$.

On the other hand, if at step S75, the amplitude (power spectrum PSQ) is minimum, the routine goes to step S78 without changes in the phases.

At step S78, the frequency components to which phase control is applied are converted into the corresponding analog signal by means of the D/A converter and are output to the speaker 45 via the speaker amplifier.

That is to say, the sound wave having the frequency components generated from the speaker 45 through the drive control at the step S78 of FIG. 16 serves to interfere with the air intake sound having the same frequency components so as to attenuate the air intake sound wave. Since the major part of the air intake sound wave is air intake pulsation noise, and the power spectrum PS provided at step S74 is accommodated to the frequency range of the air intake pulsations, it can be estimated that the air intake pulsations themselves detected by the airflow meter 10 would be attenuated if the sound wave generated from the airflow meter 10 causes the air intake pulsation noise to be reduced.

Then, in a case where the attenuation of the air intake pulsation noise detected by the airflow meter 10 is not sufficient, it is determined that the phase of the sound wave generated from the speaker 45 is not accurately opposite in phase with respect to the air intake sound wave. Hence, the phase of the sound wave generated from the speaker 45 is gradually varied so as to search for the phase state at which the effect of attenuation for the air intake pulsation can most effectively be achieved.

FIG. 17 shows a process for extracting the frequency components for the cancellation sound wave from the air intake pulsation detected by the airflow meter 10 in the ninth embodiment.

That is to say, at step S91, the CPU reads the digital converted signal of the output AFM derived from the A/D converter 52.

At step S94, the CPU determines whether the digital signal at step S91 falls within the predetermined sampling window.

If the CPU determines that the digital signal is within the predetermined sampling window at step S92, the routine goes to step S93.

At the step S93, the CPU sequentially stores into the RAM the output signal AFM of the airflow meter 10 as data $MQ_n$ (n=1, 2, 3, . . . ).

On the other hand, if the CPU determines that the signal exceeds the sampling window, the routine goes to step S95 in which the stored data $MQ_n$ at the previous sampling window are cleared.

Referring to step S94 of FIG. 17, the CPU extracts the frequency components in a predetermined frequency band (for example, 70 Hz through 300 Hz) on the basis of the data $MQ_n$ derived at step S93 to provide the power spectrum PSQ.

It is noted that the above-described frequency range corresponds to the frequency range of the air intake pulsation. It is also noted that, in the flowchart of FIG. 16, in the power spectrum PS of the output of the microphone 46, the same frequency range is adopted.

It will be appreciated that although, in the ninth embodiment, the optimum phase is achieved on the basis of the air intake pulsation detected by the airflow meter 10 in the active noise reducing apparatus in which the sound wave for canceling the air intake pulsation noise on the basis of the result of the detection by means of the microphone 46 is generated, canceling of air intake noise cannot be sufficiently achieved unless the amplitude of the sound wave generated from the speaker 45 is approximately equal to that of the air intake pulsation noise, even if their phases are appropriate.

Hence, in the tenth embodiment, an optimum amplitude can be obtained on the basis of the air intake pulsation detected by the airflow meter 10.

Figure 18:
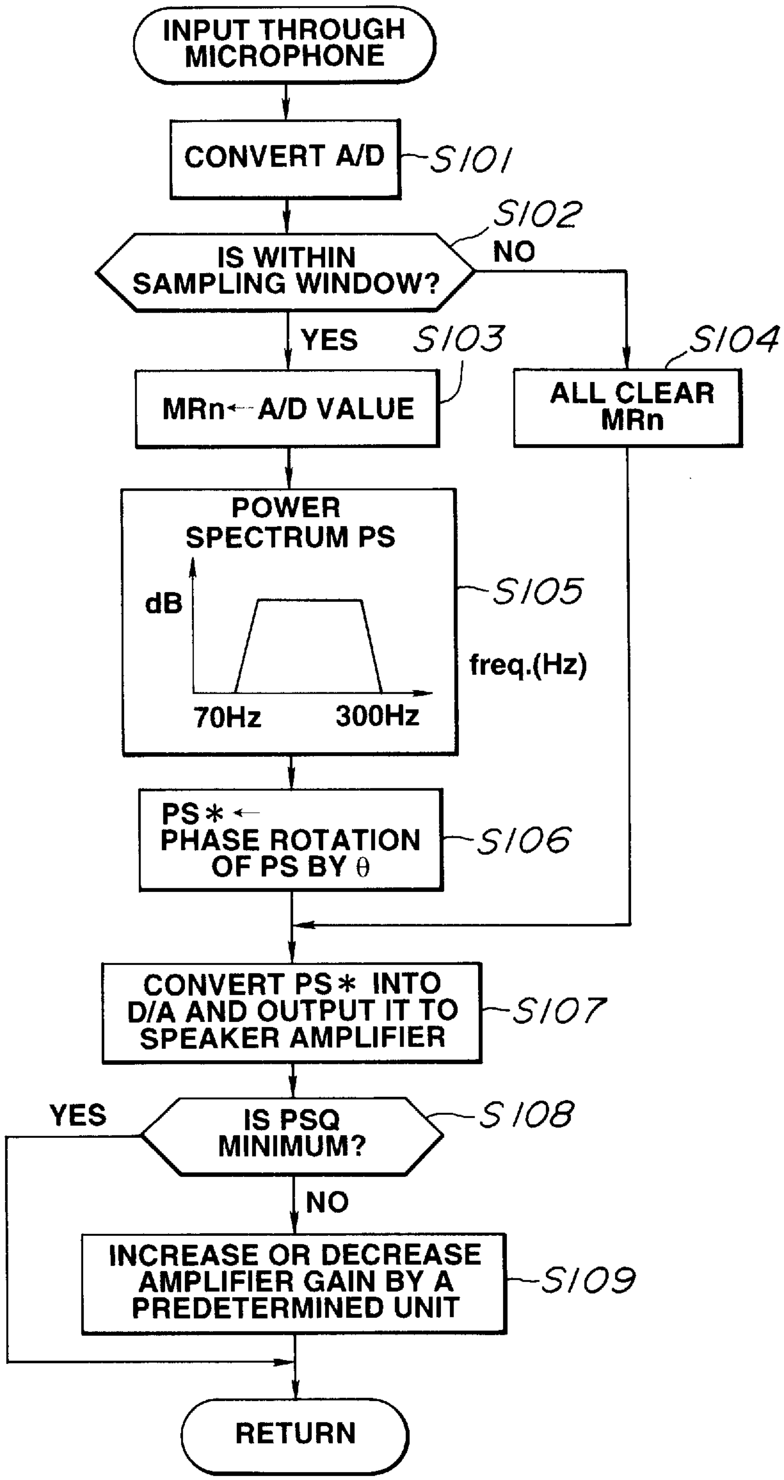
FIG. 18 is an operational flowchart indicating the active noise reduction control executed in the tenth embodiment shown in FIG. 15.

FIG. 18 shows an operational flowchart executed in the control unit 9 in the tenth embodiment of the active noise reducing apparatus according to the present invention.

In the flowchart shown In FIG. 18, at steps from a step S101 through S107, the frequency components corresponding to the air intake pulsation noise are extracted through frequency analysis of the output signal of the microphone 46, fixed phase deviations (for example, typically 180°) for the extracted frequency components are carried out, and the sound wave having the extracted frequency components is output through the speaker amplifier 55 (refer to FIG. 8).

Detailed explanations for the steps S101 through S107 are herein omitted.

Then, at step S108, the CPU determines whether the amplitude (power spectrum PSQ) of the air intake pulsation derived at step S94 of FIG. 17 is minimum. If No at step S108, the routine goes to step S109 in which the gain of the speaker amplifier 55 is adjusted gradually in a direction such that the amplitude of the air intake pulsation becomes lower.

In the tenth embodiment, the control unit determines that the amplitude set on the basis of the result of detection by means of the microphone 46 is insufficient and varies the amplitude of the sound wave generated from the speaker 45 so that a sound wave which serves to reduce the air intake pulsation noise as effectively as possible can be generated from the speaker 45.

It is noted that the combination of the ninth and tenth embodiments is possible. For example, the flowcharts of FIGS. 16, 17, and 18 are executed separately. That is to say, after the phase of the generated sound wave is adjusted on the basis of the result of detection by means of the airflow meter 10, the gain of the speaker amplifier 56 connected to the speaker 45, and therefore the amplitude of the sound wave generated from the speaker 45 is adjusted on the basis of the result of the detection by means of the airflow meter 10.

Alternatively, the frequency of the sound wave generated from the speaker 45 may be adjusted, rather than the phase and/or the amplitude.

Furthermore, the positional relationship between the microphone 46 and airflow meter 10 shown in FIG. 15 may be reversed. That is to say, the airflow meter 10, the speaker 45, and the microphone 46 may be arranged in this order on the air intake system with respect to its upstream direction. The result of driving the speaker 45 to attenuate the air intake pulsation based on the result of detection by means of the airflow meter 10 may be evaluated on the basis of the result of detection by means of the microphone 46 so that either or both of the phase and amplitude of the sound wave generated from the speaker 45 may be adjusted.

Although the air intake noise is detected within the engine air intake system and the noise reduction is carried out within the air intake system, microphones may be disposed within the passenger compartment, the effect of canceling the air intake noise on the basis of the result of detections of the microphones may be evaluated, and the characteristics (phase, amplitude, and/or frequency) of the sound wave generated within the air intake system may be adjusted on the basis of the result of evaluation.

While the present invention has been disclosed in terms of the preferred embodiments in order to facilitate better understanding thereof, It should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. An active noise reducing apparatus for an automotive vehicle, comprising:

air intake sound wave monitoring means, disposed in an air intake system of a vehicular engine, for monitoring an air intake sound wave generated in the air intake system from air intake noise and outputting a detection signal representative of the air intake sound wave;

sound wave characteristic setting means for setting a frequency, an amplitude, and a phase of a noise-reducing sound wave on the basis of said detection signal derived from said air intake sound wave monitoring means;

sound wave generating means for generating the noise-reducing sound wave on the basis of the frequency, the amplitude, and the phase set by said sound wave characteristic setting means, and interfering with the air intake sound wave so as to reduce the air intake noise; and acoustic-to-electrical transducing means for generating a signal representative of a sound wave remaining after interference of the intake sound wave, said air intake sound wave monitoring means being disposed within an air intake duct of the air intake system of the vehicular engine, the air intake duct being located upstream of an engine throttle valve, said sound wave generating means comprising electrical-to-acoustic energy transducing means, disposed adjacent to an air cleaner of the intake air system, for converting an electric signal into a corresponding acoustic signal, and said sound wave characteristic setting means comprising:

1) analog-to-digital converting means for converting the electric signal derived from said acoustic-to-electrical energy transducing means into a corresponding digital signal;

2) sampling means for sampling the electric signal derived from said acoustic-to-electrical energy transducing means before the analog-to-digital conversion by said analog-to-digital converting means within a predetermined sampling window and storing the sampled electric signals sequentially into a memory as digital discrete data $MR_n$ (n=1, 2, 3, . . . n);

3) first frequency analyzing means for carrying out a Fourier transform for the stored n-th number of digital data to provide a first frequency power spectrum (PSI);

4) first filtering means for filtering frequency components in the first frequency power spectrum PS1 so as to extract the frequency components in a first predetermined frequency band;

5) first phase controlling means for providing a phase deviation of a first predetermined angle θ1 for the extracted frequency components in the first predetermined frequency band;

6) second frequency analyzing means for carrying out a Fourier transform for the stored n-th number of digital data $MR_n$ a second time to provide a second frequency power spectrum (PS2);

7) second filtering means for filtering frequency components in the second frequency power spectrum PS2 so as to extract the frequency components in a second predetermined frequency band from the second frequency power spectrum PS2;

8) second phase controlling means for providing a phase deviation of a second predetermined angle θ2 for the extracted frequency components in said second predetermined frequency band; and 9) synthesizing means for synthesizing and converting each extracted frequency component into a single electric signal, the electric signal being supplied to said electrical-to-acoustic energy transducing means.

2. An active noise reducing apparatus for an automotive vehicle as claimed in claim 1, wherein said first predetermined frequency band ranges from 80 Hz to 150 Hz and said second predetermined frequency band ranges from 150 Hz to 300 Hz.

3. An active noise reducing apparatus for an automotive vehicle as claimed in claim 2, wherein said first and second predetermined angles θ1 and θ2 are fixed to 180°.

4. An active noise reducing apparatus for an automotive vehicle as claimed in claim 2, further comprising an airflow meter which is constructed and arranged so as to detect an intake air quantity Qa sucked into the engine and wherein said first and second predetermined angles θ1 and θ2 are varied according to the intake air quantity Qa detected by the airflow meter.

5. An active noise reducing apparatus for an automotive vehicle as claimed in claim 2, further comprising:

an airflow meter which is constructed and arranged in the intake air system of the vehicular engine so as to detect an intake air quantity Qa sucked into the engine;

engine revolution speed determining means for determining an engine revolution speed Ne on the basis of an output signal from an engine crankshaft angular displacement sensor; and intake air stream velocity determining means for determining an intake air stream velocity Qv on the basis of the intake air quantity Qa detected by the airflow meter and the engine revolution speed Ne, wherein said first and second predetermined angles θ1 and θ2 are varied according to the determined intake air stream velocity Qv.

6. An active noise reducing apparatus for an automotive vehicle, comprising:

air intake sound wave monitoring means, comprising an air flow meter disposed in an air intake system of a vehicular engine, for monitoring an air intake sound wave generated in the air intake system from air intake noise and outputting a detection signal representative of the air intake sound wave;

sound wave characteristic setting means for setting a frequency, an amplitude, and a phase of a noise-reducing sound wave on the basis of said detection signal derived from said air intake sound wave monitoring means;

sound wave generating means for generating the noise-reducing sound wave on the basis of the frequency, the amplitude, and the phase set by said sound wave characteristic setting means, and interfering with the air intake sound wave so as to reduce the air intake noise; and acoustic-to-electrical transducing means for generating a signal representative of a sound wave remaining after interference of the intake sound wave, said air intake sound wave monitoring means being disposed within an air intake duct of the air intake system of the vehicular engine, the air intake duct being located upstream of an engine throttle valve, said sound wave generating means comprising electrical-to-acoustic energy transducing means, disposed adjacent to an air cleaner of the intake air system, for converting an electric signal into a corresponding acoustic signal, and said sound wave characteristic setting means comprising:

1) analog-to-digital converting means for converting the electric signal derived from said acoustic-to-electrical energy transducing means into a corresponding digital signal;

2) sampling means for sampling the electric signal derived from said acoustic-to-electrical energy transducing means before the analog-to-digital conversion by said analog-to-digital converting means within a predetermined sampling window and storing the sampled electric signals sequentially into a memory as digital discrete data $MQ_n$ (n=1, 2, 3, . . . n);

3) engine revolution speed determining means for determining an engine revolution speed Ne on the basis of an output signal from an engine crankshaft angular displacement sensor;

4) setting means for setting a center frequency $f_0$ from the engine revolution speed Ne which is correlated to a frequency of intake air pulsation;

5) frequency analyzing and filtering means for extracting frequency components of the output signal of the airflow meter in a predetermined frequency bandwidth with the center frequency $f_0$ as a center;

6) phase controlling means for providing a phase deviation of θ for the extracted frequency components; and 7) converting means for converting the phase deviated frequency components into a corresponding electric signal, the electric signal being supplied to said electrical-to-acoustic energy transducing means.

7. An active noise reducing apparatus for an automotive vehicle, comprising:

air intake sound wave monitoring means, disposed in an air intake system of a vehicular engine, for monitoring an air intake sound wave generated in the air intake system from air intake noise and outputting a detection signal representative of the air intake sound wave;

sound wave characteristic setting means for setting a frequency, an amplitude, and a phase of a noise-reducing sound wave on the basis of said detection signal derived from said air intake sound wave monitoring means;

sound wave generating means for generating the noise-reducing sound wave on the basis of the frequency, the amplitude, and the phase set by said sound wave characteristic setting means, and interfering with the air intake sound wave so as to reduce the air intake noise; and acoustic-to-electrical transducing means for generating a signal representative of a sound wave remaining after interference of the intake sound wave, said air intake sound wave monitoring means being disposed within an air intake duct of the air intake system of the vehicular engine, the air intake duct being located upstream of an engine throttle valve, said sound wave generating means comprising electrical-to-acoustic energy transducing means, disposed adjacent to an air cleaner of the intake air system, for converting an electric signal into a corresponding acoustic signal, and further comprising an airflow meter which is constructed and arranged in the intake air system of the vehicular engine so as to detect an intake air quantity Qa drawn into the engine, and wherein said sound wave characteristic setting means comprises:

1) analog-to-digital converting means for converting the electric signal derived from said acoustic-to-electrical energy transducing means into a corresponding digital signal;

2) sampling means for sampling the electric signal derived from said acoustic-to-electrical energy transducing means before the analog-to-digital conversion by said analog-to-digital converting means within a predetermined sampling window and storing the sampled electric signals sequentially into a memory as digital discrete data $MQ_n$ (n=1, 2, 3, . . . n);

3) engine revolution speed determining means for determining an engine revolution speed Ne on the basis of an output signal from an engine crankshaft angular displacement sensor;

4) setting means for measuring a period $Tf_Q$ of a variation in a detected intake air quantity Qa of the airflow meter and setting a center frequency $f_0$ from the measured period $Tf_Q$;

5) frequency analyzing and filtering means for extracting frequency components of the output signal of the airflow meter in a predetermined frequency bandwidth with the center frequency $f_0$ as a center;

6) phase controlling means for providing a phase deviation of θ for the extracted frequency components; and 7) converting means for converting the phase deviated frequency components into a corresponding electric signal, the electric signal being supplied to said electrical-to-acoustic energy transducing means.

8. An active noise reducing apparatus for an automotive vehicle, comprising:

air intake sound wave monitoring means, disposed in an air intake system of a vehicular engine, for monitoring an air intake sound wave generated in the air intake system from air intake noise and outputting a detection signal representative of the air intake sound wave;

sound wave characteristic setting means for setting frequency, an amplitude, and a phase of a noise-reducing sound wave on the basis of said detection signal derived from said air intake sound wave monitoring means;

sound wave generating means for generating the noise-reducing sound wave on the basis of the frequency, the amplitude, and the phase set by said sound wave characteristic setting means, and interfering with the air intake sound wave so as to reduce the air intake noise; and acoustic-to-electrical transducing means for generating a signal representative of a sound wave remaining after interference of the intake sound wave, said air intake sound wave monitoring means being disposed within an air intake duct of the air intake system of the vehicular engine, the air intake duct being located upstream of an engine throttle valve, said sound wave generating means comprising electrical-to-acoustic energy transducing means, disposed adjacent to an air cleaner of the intake air system, for converting an electric signal into a corresponding acoustic signal, and further comprising an airflow meter which is constructed and arranged in a part of the engine intake air system which is located downstream of said electrical-to-acoustic energy transducing means so as to detect an intake air quantity Qa sucked into the engine and wherein said sound wave characteristic setting means comprises:

1) first analog-to-digital converting means for converting the electric signal derived from said acoustic-to-electrical energy transducing means into a corresponding digital signal;

2) first sampling means for sampling the electric signal derived from said acoustic-to-electrical energy transducing means before the analog-to-digital conversion by said first analog-to-digital converting means within a predetermined sampling window and storing the sampled electric signals sequentially into a first memory as first digital discrete data $MR_n$ (n=1, 2, 3, . . . n);

3) first frequency analyzing means for carrying out a Fourier transform for the stored n-th number of the first digital discrete data $MR_n$ to provide a first frequency power spectrum PS;

4) first filtering means for filtering frequency components in the first frequency power spectrum PS in a first predetermined frequency band so as to extract the frequency components in said first predetermined frequency band from the first power spectrum PS;

5) second analog-to-digital converting means for converting an output signal AFM from said airflow meter into a corresponding digital signal;

6) second sampling means for sampling the output signal AFM from said airflow meter within said predetermined sampling window before conversion of the output signal AFM into the digital signal by said second analog-to-digital converting means and storing the sampled output signal AFM of the airflow meter into a second memory as second digital discrete data $MQ_n$ (n=1, 2, 3, . . . n);

7) second frequency analyzing means for carrying out a Fourier transform for the stored n-th number of the second digital discrete data $MQ_n$ to provide a second frequency power spectrum PSQ;

8) second filtering means for filtering frequency components in a second predetermined frequency band so as to extract the frequency components in said second predetermined frequency band from the second frequency power spectrum PS2;

9) determining means for determining whether an amplitude of any one of the frequency components extracted by said second filtering means in the second frequency power spectrum PSQ which is the same frequency component as that of the frequency components extracted by said first filtering means in the first frequency power spectrum PS is smallest;

10) phase deviating means for providing a further phase deviation $\Delta\theta$ for the frequency component in the first frequency power spectrum PS when said determining means determines that the amplitude of any one of the frequency components extracted by said second filtering means in the second frequency power spectrum PSQ which is the same frequency component as that of the frequency components extracted by said first filtering means in the first frequency power spectrum PS is not smallest and for providing a 180° phase deviation for the frequency components in the first frequency power spectrum PS when said determining means determines that the amplitude of any one of the frequency components extracted by said second filtering means in the second frequency power spectrum PSQ which is the same frequency component as that of the frequency components extracted by said first filtering means in the first frequency power spectrum PS is smallest; and 11) synthesizing and converting means for synthesizing and converting the frequency components under phase deviation into a single electric signal, said electric signal being supplied to said electrical-to-acoustic energy transducing means.

9. An active noise reducing apparatus for an automotive vehicle as claimed in claim 8, wherein said electrical-to-acoustic energy transducing means comprises a gain adjustable amplifier and a speaker, said speaker being installed so as to face against the air cleaner, and wherein, when said determining means determines that the amplitude of any one of the frequency components extracted by said second filtering means in the second frequency power spectrum PSQ which is the same frequency component as that of the frequency components extracted by said first filtering means in the first frequency power spectrum PS is not smallest, said sound wave characteristic setting means adjusts the gain of said amplifier so that the amplitude of the intake air pulsation detected by said airflow meter becomes smaller.

10. An active noise reducing apparatus for an automotive vehicle as claimed in claim 9, wherein, when said determining means determines that the amplitude of any one of the frequency components extracted by said second filtering means in the second frequency power spectrum PSQ which is the same frequency component as that of the frequency components extracted by said first filtering means in the first frequency power spectrum PS is not smallest, said sound wave characteristic setting means adjusts the frequency of the electric signal supplied to said speaker via said rain adjustable amplifier.

11. An active noise reducing apparatus for an automotive vehicle as claimed in claim 10, wherein said predetermined frequency band in the first frequency power spectrum PS ranges from 70 to 300 Hz.

12. An active noise reducing apparatus for an automotive vehicle as claimed in claim 11, wherein said predetermined sampling window is dependent on a bit number and handling capability of the stored data treated by said Fourier transform.

13. An active air intake noise reducing apparatus for an automotive vehicle, comprising:

an air intake signal generator for generating an air intake signal representative of an air intake quantity;

a signal processor for generating a cancellation signal having a frequency, amplitude and phase for canceling the air intake signal;

a sound wave generator for generating a cancellation sound wave in accordance with the cancellation signal to cancel an air intake sound wave; and a cancellation monitor for generating a monitor signal representative of a sound wave remaining after cancellation of the air intake sound wave by the cancellation sound wave, said signal processor including means for correcting said cancellation signal in accordance with said monitor signal, comprising:

a sampler for sampling the monitor signal within a predetermined sampling window and for storing the sampled electric signals sequentially into a memory as discrete data $MR_n$ (n=1, 2, 3, . . . n);

first frequency analyzing means for performing a Fourier transform for the stored n-th number of discrete data to provide a first frequency power spectrum (PS1):

first filtering means for filtering frequency components in the first frequency Power spectrum PS1 to extract frequency components in a first predetermined frequency band;

first phase control means for providing a phase deviation of a first predetermined angle $\theta 1$ for extracted frequency components in the first predetermined frequency band;

second frequency analyzing means for performing a Fourier transform for the stored n-th number of discrete data $MR_n$ to provide a second frequency power spectrum (PS2);

second filtering means for filtering frequency components in the second frequency power spectrum PS2 to extract frequency components in a second predetermined frequency band;

second phase control means for providing a phase deviation of a second predetermined angle θ2 for the extracted frequency components in said second predetermined frequency band; and synthesizing means for synthesizing and converting each extracted frequency component into a correction electric signal and providing the correction signal to the sound wave generator.

14. An active noise reducing apparatus for an automotive vehicle as claimed in claim 13, wherein said air intake signal generator comprises an airflow meter disposed in an air intake of said automotive vehicle.

15. An active noise reducing apparatus for an automotive vehicle as claimed in claim 13, further comprising activation means for activating said noise reducing apparatus in accordance with a predetermined engine driving condition.

16. An active noise reducing apparatus for an automotive vehicle as claimed in claim 15, wherein the predetermined engine driving condition comprises an engine revolution speed not less than 2000 rpm and an engine throttle opening angle variation rate of approximately 30°/sec.

17. An active noise reducing apparatus for an automotive vehicle as claimed in claim 13, wherein said signal processor comprises:

means for measuring a number of zero values of a first-order differential of the air intake signal within a time period; and means for setting a frequency of said cancellation signal in accordance with said number of zero values.

18. An active noise reducing apparatus for an automotive vehicle as claimed in claim 13, wherein said sound wave generator is disposed within a passenger compartment of said vehicle.

19. An active noise reducing apparatus for an automotive vehicle as claimed in claim 13, wherein said sound wave generator is disposed within an air intake of an engine of said vehicle.

20. An active noise reducing apparatus for an automotive vehicle as claimed in claim 13, wherein said signal processor comprises a peak hold circuit for holding a peak value of the air intake signal for a duration corresponding to a predetermined crankshaft angular displacement, and wherein the signal processor sets the amplitude of the cancellation signal in accordance with the peak value of the air intake signal.

21. An active noise reducing apparatus for an automotive vehicle as claimed in claim 13, wherein the cancellation monitor comprises at least one acoustic to electric transducer disposed in a passenger compartment of said vehicle.

22. An active noise reducing apparatus for an automotive vehicle as claimed in claim 13, wherein the cancellation monitor comprises at least one acoustic to electric transducer disposed in an air intake of an engine of said vehicle.

23. An active noise reducing apparatus for an automotive vehicle as claimed in claim 22, wherein the sound wave generator comprises a speaker disposed adjacent to an air cleaner of an air intake of an engine of said vehicle.

24. An active noise reducing apparatus for an automotive vehicle as claimed in claim 13, wherein the cancellation monitor comprises at least one acoustic to electric transducer disposed in an air intake of an engine of said vehicle upstream of a throttle valve of said engine, and wherein the sound wave generator comprises a speaker disposed adjacent to an air cleaner of an air intake of an engine of said vehicle.

25. An active noise reducing apparatus for an automotive vehicle as claimed in claim 13, wherein said first predetermined frequency band ranges from 80 Hz to 150 Hz and said second predetermined frequency band ranges from 150 Hz to 300 Hz.

26. An active noise reducing apparatus for an automotive vehicle as claimed in claim 13, wherein said first and second predetermined angles are fixed at 180°.

27. An active noise reducing apparatus for an automotive vehicle as claimed in claim 13, wherein said air intake signal generator comprises an airflow meter for generating an air intake signal representative of an air intake mass flow quantity Qa, and wherein said first and second predetermined angles are varied in accordance with said air intake signal.

28. An active noise reducing apparatus for an automotive vehicle as claimed in claim 13, wherein said air intake signal generator comprises an airflow meter for generating an air intake signal representative of an air intake mass flow quantity Qa, and wherein said active noise reducing apparatus further comprises:

an angular displacement sensor for generating an angular displacement signal representative of angular displacement of a crankshaft of an engine of said vehicle;

means for determining an engine revolution speed from said angular displacement signal; and means for determining an air intake air stream velocity from engine revolution speed and a detected air intake mass flow quantity Qa, and wherein said first and second predetermined angles are varied in accordance with said air intake airstream velocity.

29. An active noise reducing apparatus for an automotive vehicle as claimed in claim 13, wherein said air intake signal generator comprises an airflow signal generator for generating an air intake signal representative of an air intake mass flow quantity Qa, and wherein said means for correcting said cancellation signal comprises:

a sampler for sampling the monitor signal within a predetermined sampling window and storing the sampled electric signals sequentially into a memory as discrete data $MQ_n$ (n=1, 2, 3, . . . n);

engine revolution speed determining means for determining an engine revolution speed Ne in accordance with an angular displacement signal from an engine crankshaft angular displacement sensor;

setting means for setting a center frequency to a value $f_0$ associated with the engine revolution speed Ne;

frequency analyzing and filtering means for extracting frequency components of the airflow signal in a predetermined frequency bandwidth having said center frequency $f_0$;

a phase controller for providing a phase deviation of θ for extracted frequency components; and a converter for converting phase deviated frequency components into a corresponding electric signal, and for supplying the electric signal to the sound wave generator.

30. An active noise reducing apparatus for an automotive vehicle as claimed in claim 13, wherein said air intake signal generator comprises an airflow signal generator for generating an air intake signal representative of an air intake mass flow quantity Qa, and wherein said means for correcting said cancellation signal comprises:

a sampler for sampling the monitor signal within a predetermined sampling window and storing the sampled electric signals sequentially into a memory as discrete data $MQ_n$ (n=1, 2, 3, . . . n);

engine revolution speed determining means for determining an engine revolution speed Ne on the basis of an angular displacement signal from an engine crankshaft angular displacement sensor;

setting means for measuring a period $Tf_Q$ of a variation in a detected air mass flow quantity Qa and for setting a center frequency $f_0$ from the measured period $Tf_Q$;

frequency analyzing and filtering means for extracting frequency components of the airflow signal in a predetermined frequency bandwidth having a center frequency $f_0$;

a phase controller for determining a phase deviation of θ of extracted frequency components of the airflow signal; and a convertor for converting phase deviated frequency components into a corresponding electric signal, and supplying the electric signal to said sound wave generator.

31. An active noise reducing apparatus for an automotive vehicle as claimed in claim 13, wherein said air intake signal generator comprises an airflow signal generator for generating an air intake signal representative of an air intake mass flow quantity Qa, and wherein said means for correcting the cancellation signal comprises:

a first sampler for sampling the monitor signal within a predetermined sampling window and for storing sampled signals sequentially into a first memory as first discrete data $MR_n$ (n=1, 2, 3, . . . n);

a first frequency analyzer for performing a Fourier transform for the stored n-th number of the first discrete data $MR_n$ to provide a first frequency power spectrum PS;

a first filter for filtering frequency components of the first frequency power spectrum PS in a first predetermined frequency band to extract the frequency components of the first power spectrum PS in the first predetermined frequency band;

a second sampler for sampling the air intake signal within the predetermined sampling window and storing a sampled signal in a second memory as second discrete data $MQ_n$ (n=1, 2, 3, . . . n);

a second frequency analyzer for performing a Fourier transform for the stored n-th number of the second digital discrete data $MQ_n$ to provide a second frequency power spectrum PSQ;

a second filter for filtering frequency components in a second predetermined frequency band to extract the frequency components of the second frequency power spectrum PS2 in the second predetermined frequency band;

means for determining whether an amplitude of an extracted frequency component extracted from the first frequency power spectrum PS and the second frequency power spectrum PS2 is smaller in the second frequency power spectrum PS2;

a phase deviator for providing a phase deviation Δθ for an extracted frequency component in the first frequency power spectrum PS when the amplitude of the extracted frequency component extracted from the first frequency power spectrum PS and the second frequency power spectrum PS2 is not smaller in the second frequency power spectrum PS2, and for providing a 180° phase deviation for an extracted frequency component in the first frequency power spectrum PS when the amplitude of the extracted frequency component extracted from the first frequency power spectrum PS and the second frequency power spectrum PS2 is smaller in the second frequency power spectrum PS2; and means for synthesizing and converting phase deviated extracted frequency components into a single signal and supplying the single signal to the sound wave generator.

32. An active noise reducing apparatus for an automotive vehicle as claimed in claim 31, wherein the sound wave generator comprises a gain adjustable amplifier and a speaker facing an air cleaner, and wherein the signal processor adjusts the gain of the amplifier when the amplitude of the extracted frequency component extracted from the first frequency power spectrum PS and the second frequency power spectrum PS2 is not smaller in the second frequency power spectrum PS2 to reduce the amplitude of the signal from the air intake signal generator.

33. An active noise reducing apparatus for an automotive vehicle as claimed in claim 31, wherein said predetermined frequency band of the first frequency power spectrum PS ranges from 70 to 300 Hz.

* * * * *